(12) United States Patent
Domenici (10) Patent No.: US 12,083,264 B2
(45) Date of Patent: *Sep. 10, 2024

(54) INHALATION DEVICE

(71) Applicant: Derek Domenici, Sparkill, NY (US)

(72) Inventor: Derek Domenici, Sparkill, NY (US)

( * ) Notice: Subject to any disclaimer, the term of this patent is extended or adjusted under 35 U.S.C. 154(b) by 47 days.

This patent is subject to a terminal disclaimer.

(21) Appl. No.: 17/443,206

(22) Filed: Jul. 22, 2021

(65) Prior Publication Data

US 2022/0008667 A1 Jan. 13, 2022

Related U.S. Application Data

(63) Continuation of application No. 16/151,861, filed on Oct. 4, 2018, now Pat. No. 11,103,656.

(60) Provisional application No. 62/568,581, filed on Oct. 5, 2017.

(51) Int. Cl.
| | |
|---|---|
| *A24F 40/42* | (2020.01) |
| *A24F 40/44* | (2020.01) |
| *A24F 40/46* | (2020.01) |
| *A24F 40/48* | (2020.01) |
| *A24F 40/485* | (2020.01) |
| *A61M 11/04* | (2006.01) |
| *A61M 15/00* | (2006.01) |

(Continued)

(52) U.S. Cl.
CPC ............ *A61M 11/042* (2014.02); *A24F 40/42* (2020.01); *A24F 40/44* (2020.01); *A24F 40/46* (2020.01); *A24F 40/485* (2020.01); *A61M 15/0021* (2014.02); *A61M 15/0025* (2014.02); *A61M 15/003* (2014.02); *A61M 15/0036* (2014.02); *A24F 40/10* (2020.01); *A24F 40/48* (2020.01); *A61M 15/06* (2013.01); *A61M 2205/8206* (2013.01)

(58) Field of Classification Search
CPC .......... A24F 40/10; A24F 40/42; A24F 40/44; A24F 40/46; A24F 40/48
USPC ........................................................ 131/329
See application file for complete search history.

(56) References Cited

U.S. PATENT DOCUMENTS 3,688,765 A * 9/1972 Gasaway ................ A61M 5/30
124/71
4,482,071 A 11/1984 Ishiwatari
(Continued)

FOREIGN PATENT DOCUMENTS

CN 106490693 A 3/2017

*Primary Examiner* — Russell E Sparks
(74) *Attorney, Agent, or Firm* — Lerner David LLP (57) ABSTRACT

Disclosed is an inhalation device which comprises a housing having a removable therein. The vial will contain such liquid as phyto-cannabinoids, cannabidiol, terpenoids, aromatherapy, or tetrahydrocannabinol. A conveyance tube in the housing communicate with the interior of the vial and has therein a material for conveying the distillates by capillary action to a vaporization chamber. The conveyance tube has a conically shaped head for puncturing THC membrane. The liquid in the vial to passes from the conveyance tube into a vaporization chamber. The vaporization chamber, which is also in the housing, has attached to it a heating device for vaporizing the liquid. The vaporized liquid then passes through vents in the vaporization chamber housing and within the main housing so as to be available to be drawn out through a mouthpiece which is in turn secured to the housing.

20 Claims, 11 Drawing Sheets

(51) Int. Cl.
*A24F 40/10* (2020.01)
*A61M 15/06* (2006.01)

(56) References Cited

U.S. PATENT DOCUMENTS

| | | | | |
|---|---|---|---|---|
| 4,948,009 | A * | 8/1990 | Sawatani | A23F 5/243 |
| | | | | 220/254.1 |
| 8,997,754 | B2 * | 4/2015 | Tucker | H05B 3/44 |
| | | | | 131/273 |
| 9,132,248 | B2 * | 9/2015 | Qiu | A24F 40/53 |
| 9,427,022 | B2 * | 8/2016 | Levin | A24F 40/51 |
| 9,497,993 | B2 | 11/2016 | Vallar | |
| 9,877,521 | B1 * | 1/2018 | Gillis | A24F 40/42 |
| 9,883,696 | B2 * | 2/2018 | Liu | H05B 3/04 |
| 9,936,731 | B2 * | 4/2018 | Hopps | A61M 11/042 |
| 10,004,266 | B2 * | 6/2018 | Liu | A24F 40/49 |
| 10,039,318 | B2 * | 8/2018 | Daryani | A24F 7/02 |
| 10,064,434 | B2 * | 9/2018 | Zitzke | H05B 1/02 |
| 10,172,390 | B2 * | 1/2019 | Nakano | B65B 69/0033 |
| 10,206,430 | B2 * | 2/2019 | Mironov | B29C 43/14 |
| 10,285,444 | B2 * | 5/2019 | Clemens | A24F 40/44 |
| 10,321,712 | B2 * | 6/2019 | Lipowicz | A61M 11/042 |
| 10,617,153 | B2 * | 4/2020 | Qiu | A61M 15/06 |
| 10,792,443 | B2 * | 10/2020 | Xu | A61M 11/044 |
| 11,154,670 | B2 * | 10/2021 | Saygili | A24F 40/42 |
| 2004/0043064 | A1 * | 3/2004 | Lorio | A61K 9/4891 |
| | | | | 424/452 |
| 2009/0255534 | A1 | 10/2009 | Paterno | |
| 2010/0018528 | A1 | 1/2010 | Cuzydlo | |
| 2014/0190477 | A1 * | 7/2014 | Qiu | A61M 11/042 |
| | | | | 128/202.21 |
| 2015/0040929 | A1 | 2/2015 | Hon | |
| 2015/0216237 | A1 | 8/2015 | Wensley et al. | |
| 2016/0286860 | A1 | 10/2016 | Flayler | |
| 2016/0353805 | A1 | 12/2016 | Hawes et al. | |
| 2017/0042246 | A1 | 2/2017 | Lau et al. | |
| 2017/0064997 | A1 * | 3/2017 | Murison | H02J 7/0044 |
| 2019/0001087 | A1 * | 1/2019 | Davidson | A61M 15/0091 |
| 2020/0093178 | A1 * | 3/2020 | Serventi | B29C 63/0069 |

* cited by examiner

INHALATION DEVICE

CROSS-REFERENCE TO RELATED APPLICATION

This application is a continuation of U.S. patent application Ser. No. 16/151,861, filed Oct. 4, 2018, which claims priority to U.S. Provisional Patent Application No. 62/568,581, filed Oct. 5, 2017, the contents of all of which are hereby incorporated by reference in their entirety.

FIELD OF THE INVENTION

The invention relates generally to inhalation devices and, in particular, to portable electronic vaporizing devices of the type intended to deliver medicaments, *cannabis*, phytocannabinoids, cannabidiol, marijuana, or the like to a user.

BACKGROUND

Inhalation vaporizers are quickly gaining market share from conventional combustible products as a safer alternative and/or as a means for delivering medicaments or other substances. For example, vaporizers for use with extracts of tobacco and marijuana *cannabis* allow consumption of the active ingredients of these substances and eliminate the carcinogens associated with these substances. Vaporizers are more convenient than smoking products because they can be activated for just one or two inhalations while traditional paper and leaf products are typically either single use or create a lot of waste during reuse. Also, vaporizers are a convenient and controllable means for delivering such substances as medicaments including in metered dosages. These devices are more durable when made from nonporous materials such as glass or metals which allow them to withstand significantly more abuse by users.

There have been disposable and nondisposable vaporizers. Disposable vaporizers come pre-packaged with a liquid solution containing an active ingredient. Once consumed, the entire vaporizer is thrown away. The disposing of multiple vaporizers becomes an additional burden on the environment. Refillable vaporizers typically are of higher quality than disposable vaporizers. Generally, the vaporizer is formed from many pieces, some of which are detachably coupled by well known means and by which a means for storing the vaporizable material may be replaced. Typically, the storing means or reservoir is removed and opened in situ. Afterwards, the reservoir is closed and re-secured. However, the process of manually refilling liquid solution into the reservoir can be made inconvenient and complicated by unintended spillage when trying to direct the liquid solution into a reservoir's small chamber.

Yet another concern is that the liquid is commonly stored with operational elements used for vaporization. The combination leads to the introduction of pollutants and contaminants which markedly reduce the effectiveness of the liquid and the life of the liquid.

In addition, conventional manufacturing processes can require strict timing in order to prevent leakage. A reservoir as used in such devices typically has a hole through the bottom or base wall for access by a heater during vaporizing. If the reservoir containers of such devices are not quickly plugged to create a vacuum, leakage can be significant. Some liquid solutions are oil-based and can be difficult to clean.

Another concern is that, if during use the heating element that is used to vaporize the liquid fails, the remaining liquid may be lost or become extremely inconvenient or costly to recover. Further, in vaporizers the liquid commonly is stored with the heating filaments and that storage contact of the liquid with the heating elements can seriously diminish the ability of the vaporizer to vaporize the stored liquid.

SUMMARY

Disclosed is an inhalation device of the type having a mouthpiece, is selectively activated by electrical energy, and in which a vapor is obtained from a stored liquid substance and then is deliverable to a user upon the user puffing from said inhalation. The inhalation device includes means for storing the substance and means for heating the substance. The heating means is separate from the storing means. There is also means for conveying at least a part of the substance from the storing means to the heating means. The heating means, upon receiving the substance and upon its activation produces the vapor from the substance. Means are provided for communicating the vapor from the heating means such that upon the user puffing on said inhalation device, the vapor is delivered to the user.

In a further aspect of this device the means for storing the substance comprises a vial having an opening at one end for dispensing the substance. The vial may be made of borosilicate or any other suitable material.

In another aspect, the storing means includes the vial having an opening at one end thereof for dispensing the substance and a closure for sealing the open end of the vial. The closure includes a septum and means for providing a closure cap for being disposed over the septum and about the end of the vial. The cap seals the vial opening.

Further the septum may be fixedly disposed within the vial opening.

Alternatively the closure means includes the septum disposed upon the vial opening and extending about at least a part of the exterior surface of the vial. The closure cap comprises malleable material for covering the septum and crimping the material about the septum to thereby hold the septum fixedly against said exterior side of the vial to form the cap.

In another consideration the septum has a part thereof having a reduced cross-sectional thickness and a grommet-like reinforcement about the reduced cross-sectioned thickness; the reduced thickness is disposed in registry with the vial opening.

In yet another aspect of this device, there is provided a vaporizing housing. The heating means are within said vaporizing housing. The vaporizing housing has a substance receiving aperture therethrough providing access from the exterior to the interior of the vaporizing housing. A hollow conveying tube which is open at opposed ends and has at least one laterally extending tube aperture from the conveying tube exterior into the interior of said tube for permitting the substance in said vial to enter into the conveying tube. One of the conveying tube open ends is secured to the vaporizing housing aperture for conveying the substance through substance receiving aperture and into the vaporizing housing. The conveying tube comprises means for piercing the cap and the septum at the septum reduced cross-sectional thickness. Within the conveying tube is a wicking material for conducting the substance by capillary action so that the substance in said vial being capable of entering said conveying tube through said tube aperture and being transported by capillary action through said tube aperture and into said vaporization housing.

In another aspect there are at least two laterally extending tube apertures each of different sizes so as to be able to accept stored substances of differing viscosities.

In another aspect the piercing means comprises a conically shaped piercing member and a shaft integrally formed with said conical member; said shaft having free end secured into the end of said conveying tube opposed to said end secured to said substance receiving aperture of said vaporization chamber.

In still another aspect the wicking material is made of cotton.

In still a different aspect, the wicking material is made of ceramic.

In yet a further aspect, the inhalation device comprises a device housing. The vial and the vaporizing housing are within the device housing. The device housing has an aperture from the device housing exterior into the device housing interior to permit the vapor to be drawn from the inhalation device by the user. The device housing has means for channeling the vapor from said vaporizing housing to the device housing aperture.

In still another aspect of this device, the vaporizing housing has a vapor aperture extending from the exterior of the vaporizing housing to the interior of the vaporizing housing to permit vapor produced by the heating of the substance by the heating means to leave the vaporizing housing.

In a further aspect the device housing comprises an exterior wall and at least one interior wall joined to the exterior wall. The exterior wall is spaced from the interior wall and within the device housing interior. The exterior and interior walls having a flue space. The interior wall of the device housing being open within the device housing proximate the vapor aperture in the vaporizing chamber and proximate the device housing aperture so as to define the flue space.

In still a further aspect, the interior of the device housing has a space between the vapor aperture and the device housing aperture.

In a further aspect there is a mouthpiece connected to the exterior of the device housing and engaging the device housing aperture such that the user may draw vapor accumulated within the device housing.

In addition, the device housing has a generally cylindrical shaped exterior wall and the interior surface of said device housing exterior wall defines therewith in a device housing chamber. The vaporizing housing comprises a generally cylindrical shaped exterior wall. The interior surface of the vaporizing chamber exterior wall defines therewithin a hollow vaporization chamber and so dimensioned such that the exterior surface of the vaporizing housing is spaced from the interior surface of the device housing wall. The vapor aperture is at least one slot. There is a wall closing one end of the vaporizing housing which extends substantially perpendicular to the principle axis of the vaporizing housing cylinder. The heating means comprises a heater housing which has a generally cylindrically shaped outer wall within the vaporizing housing and enclosing the opposed end of vaporizing housing opposed to said one end wall and enclosing the device housing.

In still another aspect of this device there are heating means which further comprises a heating coil of ceramic within the heater housing and responsive to the electrical power. There is a protective barrier about the ceramic to prevent the substance from damaging the ceramic.

In addition the protective barrier may be made of polypropylene fibers which are needle punched to form a strong and impermeable barrier.

Alternatively the heating means can comprise a heating wire and a nonconductive armature secured within the heating housing. The heating wire is wrapped about the armature and is responsive to the electrical power.

In a further consideration the heating wire is titanium and the armature is quartz. Alternatively the heating wire is titanium and the armature is ceramic. Alternatively the heating wire is titanium and said armature is cotton.

In yet another aspect of the invention a mouthpiece connected to said exterior of said device housing and engaging said device housing aperture such that the user may draw vapor accumulated within said housing through said mouthpiece.

The inhalation device as may also have a pen-like in configuration.

DETAILED DESCRIPTION

The features of the devices herein, both as to their structure and operation, will be best understood from the accompanying drawings taken in conjunction with the accompanying written description, in which similar reference characters refer to similar parts.

Figure 1:
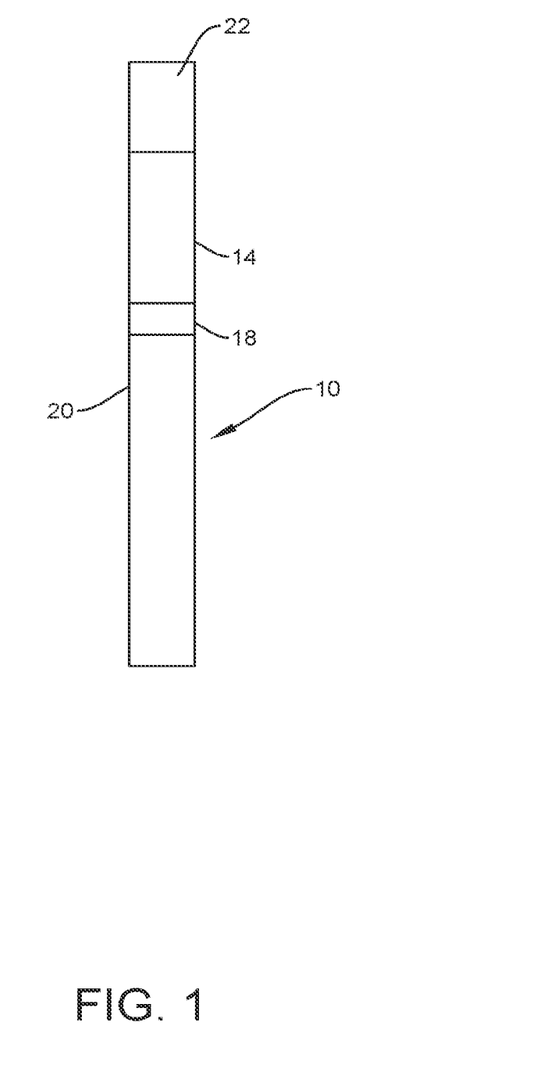
FIG. 1 is a perspective view of the inhalation devices described herein.
Figure 2:
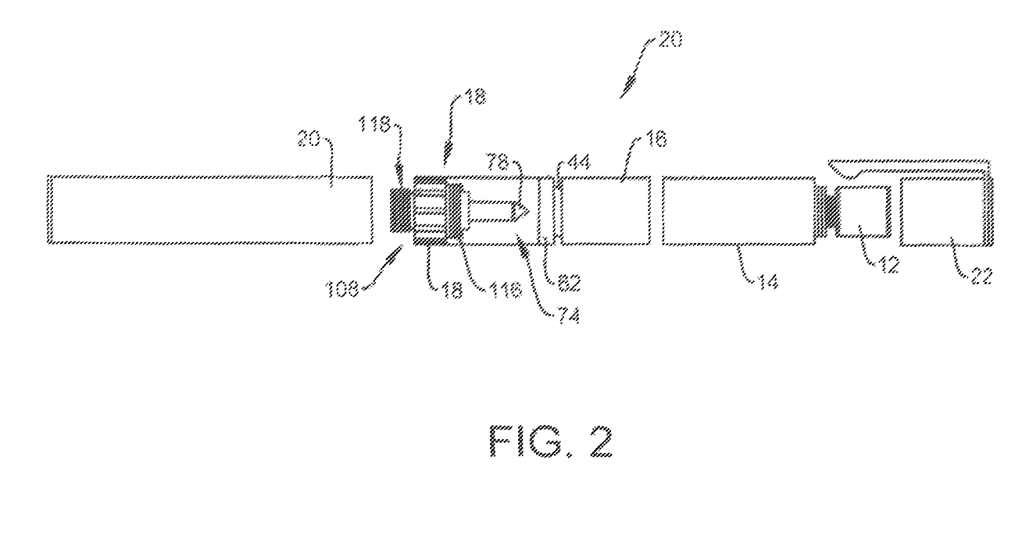
FIG. 2 is an exploded view of the devices of FIG. 1.

Described is an electronic vaporizing device for use with extracts or a distillate, such as phytocannabinoids, cannabidiol, terpenoids, aromatherapy, nicotine, or tetrahydrocannabinol. The device of this example IO (FIGS. 1, 2) has the general appearance of a pen-like device. In the alternative, the device can take any other desired configuration. The vaporizing device described here comprises a mouthpiece 12, a main housing 14 having a generally cylindrical wall for retaining therein a container or vial 16 for providing a liquid to a vaporization chamber 18. The vaporization chamber 18 has attached to it a heating device 94 for vaporizing the liquid. A battery compartment 20 coupled to the heating device 94 for providing electrical power to the heating device within the vaporization chamber 18. The mouthpiece 12 may be enclosed by a cover or pen cap 22. With the pen cap 22 in place, the entire device 10 may have the appearance of a pen-like structure.

Figure 3:
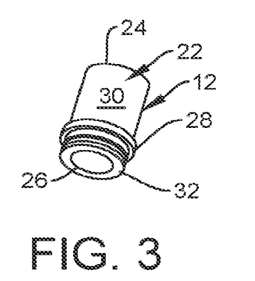
FIG. 3 is a perspective view of the mouthpiece for the device of FIG. 1.
Figure 4:
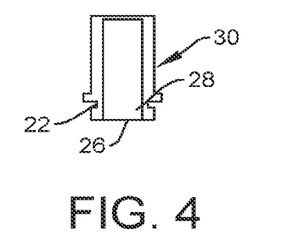
FIG. 4 is a sectional view of the mouthpiece of FIG. 3 taken along line 4-4 and looking in the direction of the arrows.
Figure 5:
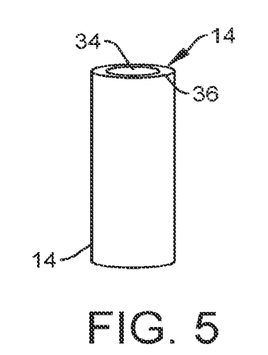
FIG. 5 is a perspective view of the main housing of FIG. 1.

The mouthpiece 12 (FIGS. 2-4) may take any convenient shape to be insertable into a user's mouth. In this example, the mouthpiece 12 is a-cylindrical hollow tube which may be made of any nonabsorbent structural material such as glass or stainless steel. The mouthpiece 12, is open into the interior at opposed ends 24, 26. An integrally formed collar 28 may extend laterally from the outer cylindrical surface 30 (FIGS. 2-4) of the mouthpiece 12 and proximate one of the ends 26. The outer wall 30 the mouthpiece 12 is threaded 32 between the collar 28 and the proximate end 26. The threaded end 32 of the mouthpiece 12 is engageable with an internally threaded wall 34 of one end 36 of the main housing 14 (FIG. 5). Instead of coupling by means of a threaded engagement, the mouthpiece 12 may also be coupled to the main housing 14 by any other known means, such as by magnets (not shown).

Figure 6:
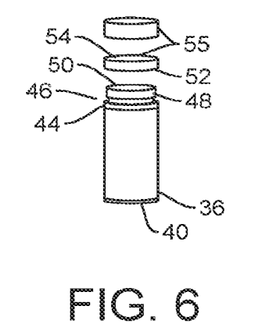
FIG. 6 is an exploded perspective view of the container of FIG. 1.
Figure 7:
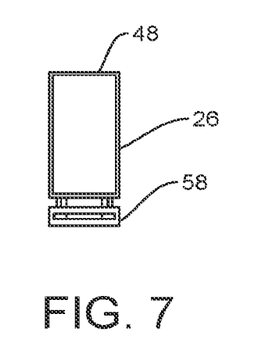
FIG. 7 is a sectional view of the container of FIG. 6.
Figure 8:
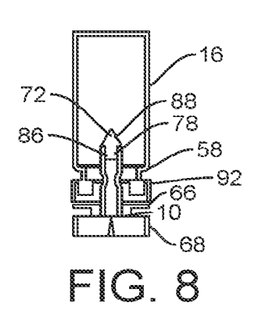
FIG. 8 is a sectional view of the container of FIG. 7 taken along line 8-8 and looking in the direction of the arrows of the container with a tube of the device of FIG. 1 inserted therein.

The glass vial 16 (FIGS. 2, 6-8) may be made of borosilicate or any other material which exhibits similar characteristics of strength and impermeability as borosilicate. The vial 16 is used to receive a liquid (not shown). The vial 16 may be made by any well known means such as by molding and dimensioned so as to fit within and be spaced from the inner surface of the cylindrical side wall 15 (FIGS. 2, 5) of the main housing 14. The cylindrical side wall 38 of the container 16 terminates in an integrally formed bottom wall 40 (FIG. 6). Adjacent the end 42 of the vial 16 opposed to the bottom wall 40 the cylindrical side wall 38 may have a radially narrowed neck 44 (FIG. 6). The container's cylindrical side wall 38, between its neck 44 and the end 42, may terminate in a lip 46 having a smaller diameter than that of the side wall 38. The lip 46 defines the end wall 48 of the vial 16. The end wall 48 is opposed to the bottom wall 40. An aperture 50 in the end wall 48 provides access into the vial 16.

Figure 9:
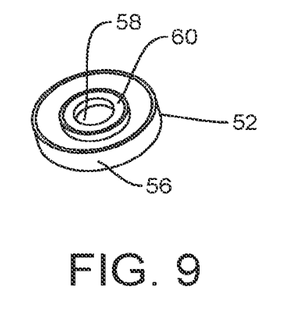
FIG. 9 is a perspective view of a-septum of the device of FIG. 1.

The end wall 48 may be enclosed by a septum or membrane 52 (FIGS. 6, 9). The septum 52 may be made of silicon, a PFSE blended rubber, or the like and may have a disk shaped cover wall 54 with an integrally formed depending skirt or lip 56. The lip 56 is so dimensioned as to engage the lip 46 of the vial 16 to thereby enclose the open end 48 of the vial 16. The disk shaped wall 54 of the membrane 52 may have a centrally disposed circular weakened or thinned portion 58 which, with the membrane 52, is disposed over the lip 46 of the vial 16, is in registry with the aperture 50 of the vial 16. Integrally formed with, the membrane cover wall 54 and within the lip 56 may be an integrally formed grommet-like thickening 60 encircling the weakened area 58. (Alternatively, the membrane 52 may be so configured as to fit within the aperture 50 in a snug fit or adhered therein by any other known means.)

Figure 10:
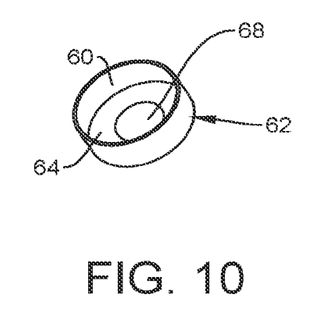
FIG. 10 is a perspective view of the cap intended to enclose the septum of the device of FIG. 1.
Figure 11:
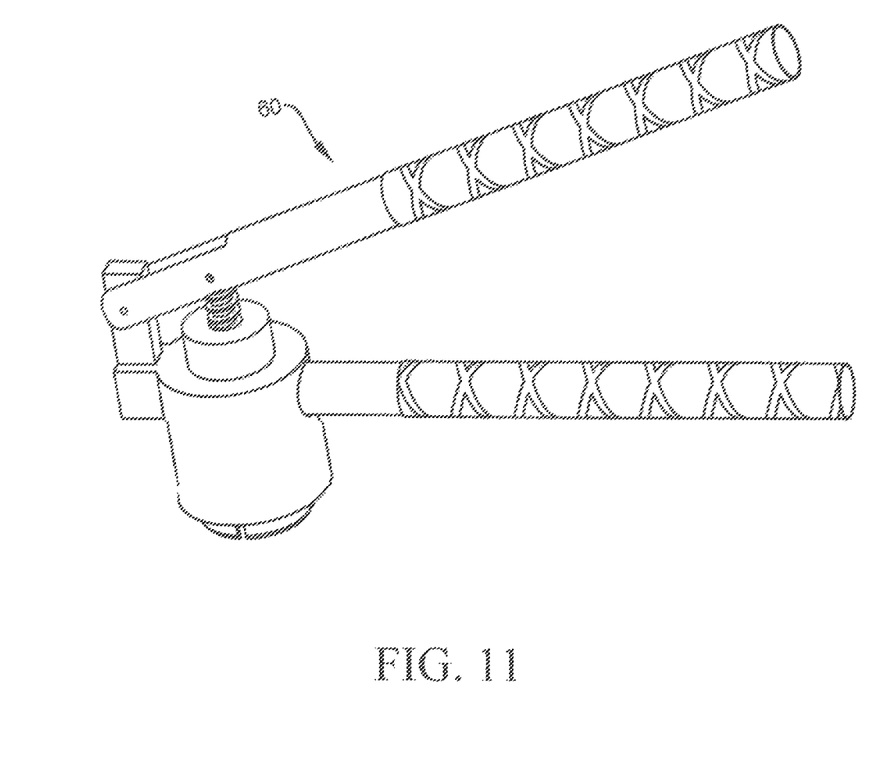
FIG. 11 is a perspective view of a crimping device.
Figure 12:
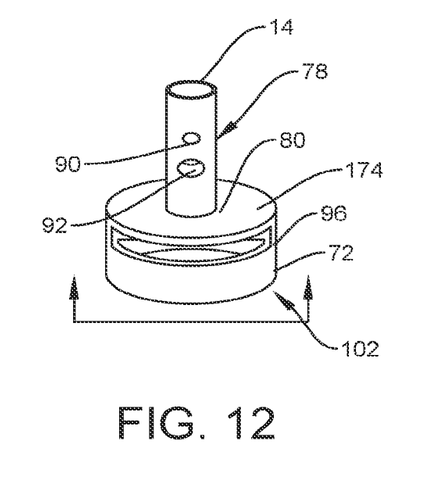
FIG. 12 is a perspective view of a heating chamber with attached tube of the device of FIG. 1.
Figure 13:
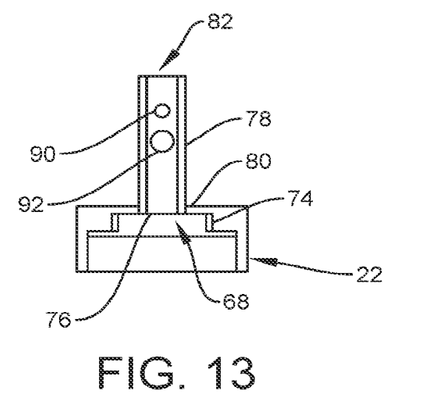
FIG. 13. Is a sectional view of the vaporization chamber and tube of FIG. 11 along lines 12-12 and looking in the direction of the arrows.

A cap 62 (FIGS. 2, 7, 10) has a disk-like cover 64 with a depending cylindrical lip 72 and a centrally disposed aperture 68. With the cap 6.2 disposed over the membrane 52, the cap aperture 68 is in registry with the weakened area 58 of the membrane 52. The cap 62 may be made of zinc, aluminum or any other material capable of being crimped into place about and into the neck 44 of the vial 16. With the cap 62 crimped into place about the neck 44 of the vial 16, the membrane 52 and the liquid in the vial 16 are sealed in place. The cap 62, may be crimped into place about the membrane 52 and the lip 58 of the vial 16 by use of a commercially available crimping tool 70 (FIG. 11) such as made by Rugao Jingtong, of Rugao city, Jiangsu, Peoples Republic of China. It may be necessary, however, to adjust the dimensions of the tool 70 as a function of the dimensions of the vial 16.

The vaporization chamber 18 (FIGS. 2, 8, 12-14) includes a generally cylindrically shaped housing 72 (FIGS. 8, 12-14) which is closed at its upper end by an integrally formed diametrically extending upper end wall 74 which is perpendicular to the major axis of the cylindrical housing 72. The upper end wall 74 has an aperture (not visible) at its radial center of the upper end wall 74 providing access into the interior of the vaporization chamber housing 72.

Figure 21:
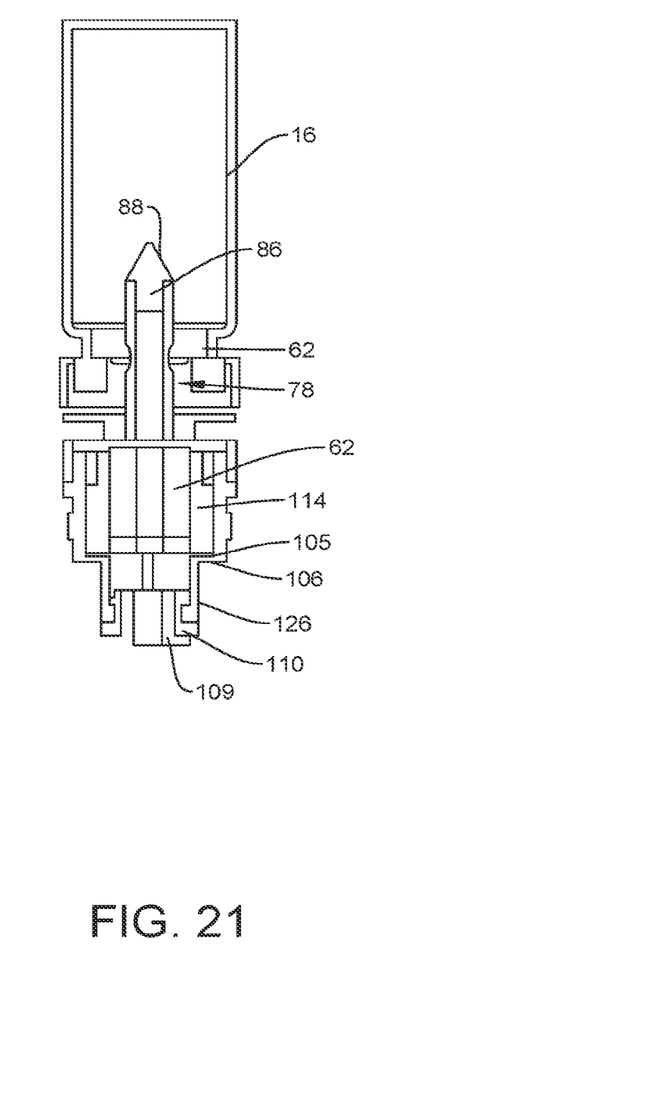
FIG. 21 is a schematic drawing of a vial secured to a conveyance tube of a vaporization chamber and vaporization chamber of the type disclosed in FIG. 16.

The vaporization chamber 18 further includes a hollow conveying tube 78 extending perpendicularly from the upper end wall 74. The tube 78 has opposed open ends 80, 82. The conveying tube 78 is attached to the upper wall 74 by one of its ends 76 being force or snug fit into the end wall aperture of the vaporization chamber housing 72. The conveying tube 78 extends perpendicularly to and from the upper end wall 74. A piercing member 84, which is of a conical shape and may be made from stainless steel, or a material exhibiting similar physical characteristics, has a solid cylindrical solid stem 86 surmounted by an integrally formed conical head 82 (FIG. 21) is inserted into and closes the tube open end 82 of the tube 78.

Figure 14:
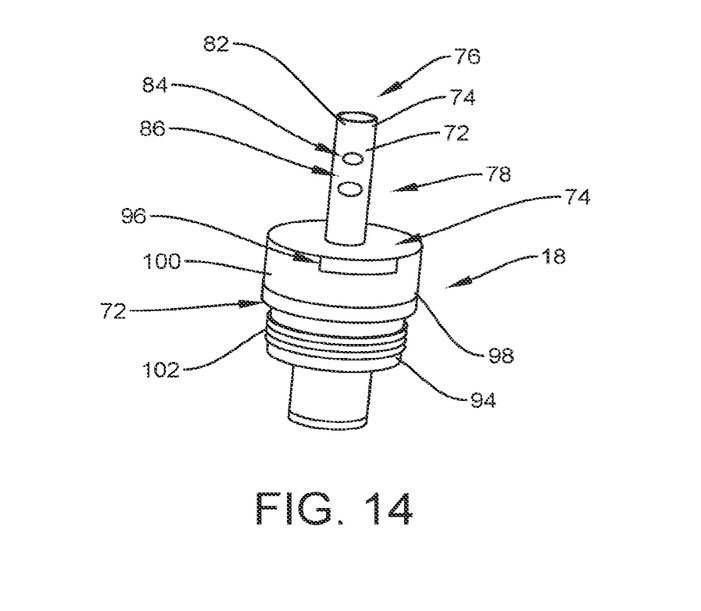
FIG. 14 is a perspective view of a the assembled vaporization chamber, tube, and heating coil.
Figure 15:
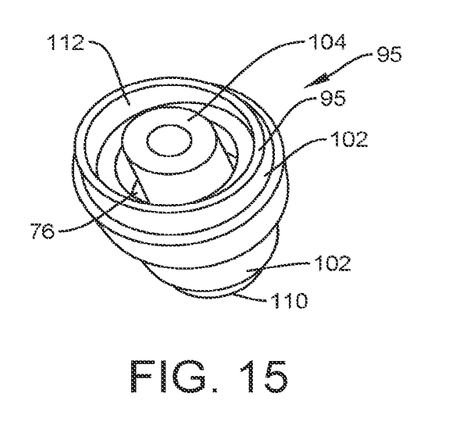
FIG. 15 is a perspective view of a heater housing without the fiber insert used in connection with the vaporization chamber of FIG. 14.
Figure 16:
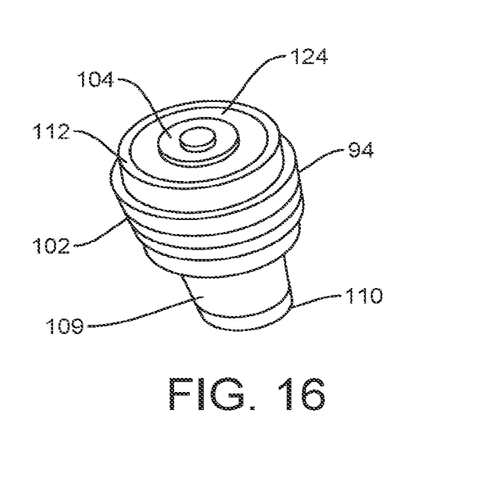
FIG. 16 is a perspective view of the heater of FIG. 15 fully assembled.

The stem 86 is so dimensioned such that it may be fixedly inserted into the open end 82 of the conveying tube 78 by a snug or force fit. The conveying tube 78 may have at least two apertures 84, 86 through its cylindrical side wall (FIGS. 8, 11-13). The apertures 84 and 86 may be of different diameters in order to accept entrance of the stored liquids. The size of each aperture 84, 86 is chosen to admit there through liquid according to the liquid's viscosity; the larger diameter aperture 86 being able to accept a more viscous liquid. Within the conveying tube 78 is a wick (not shown) which may be made of cotton, ceramic, or similar material for conducting the liquid by capillary action from the container 16 and into the vaporization chamber 18 where liquid is heated by a heating device 94 (FIGS. 15-16). The cylindrical vaporization chamber housing 72 may have a cylindrical side wall 100. There may be two apertures 96, 98 which, in this example, are circumferentially extending vents or slots 96, 98 (FIGS. 12, 14) through its cylindrical side wall 100. The bottom 101 of the vaporization chamber 18 (FIG. 12) opposed to the upper end wall 74 is open to accept the heating device 94 (FIG. 14).

The heating device 94 (FIGS. 15, 16, 21) in this example includes a heater housing 102 which may be generally cylindrical shaped and hollow and may be made of plastic or a metal and having an integrally formed base wall 106 from which extends an integrally formed hollow cylindrically shaped stem 108. The stem 108 extends coaxially with the principle axis of the heater housing 102. A heating coil 104 which may be ceramic (FIG. 21) is wrapped in a means to shield the liquid 115 to be heated from the coil 104. This protective barrier may be provided before installing the coil 104 in the housing. A wire 105 (FIG. 1) is connected to the ceramic heating coil 104 in a well known manner and extends downwardly through apertures (not visible) in the base wall 106. The stem 108 has a plug 110 which is insulated and may be made of silicon. Inserted into the insulated plug 110, and thereby electrically shielded from the housing 102, is an electrode 109 to which the wire 105 is connected. Within the open upper end 112 of the heater housing 102 is a nonwoven fiber 114. The fiber 114, in this example, is made of polypropylene fibers which are needle punched to form a strong, thick structure which is a substantially impermeable barrier to retain the liquid received from the vial 16.

The heater housing 1012 (FIG. 15) is secured to the vaporization chamber housing 72 opposed to and spaced from the chamber's upper end wall 74 by any well known means such as by an adhesive to thereby completing the vaporization chamber.

The cylindrical end 114 of the main housing 14, which is opposed to the cylindrical end 36 which receives the mouthpiece 12 (FIGS. 4-5) may be internally threaded (not visible). The external wall of the vaporization chamber housing 72 may be externally threaded 116 (FIGS. 2, 13) and so dimensioned as to engage the internal threads within the cylindrical end 114 of the main housing 14.

The end 118 of the stem end 108 of the heater housing 102 is removably connectable to the battery compartment 20 by magnets or by threading in a manner that is well known. For a magnetic connection, oppositely poled magnets may be disposed in the stem 108 and the battery compartment 20, respectively, in a well known manner. Alternatively, the stem 108 may be externally threaded to mate with, internal threads in the battery compartment 20. When the battery compartment 20 is engaged with the stem 108 and a battery is disposed within the battery compartment 20, electrical power is provided to the ceramic heating coil 104 via the electrode 109 and wire 105. The vial 16 and vaporization chamber 18 are disposed within and spaced from the interior walls of the main housing 14. The main housing 14 is sealed except for the port into the mouthpiece 12 and has a viewing window 13 by which the user can view the contents of the vial 16.

In use, the vial 16 is pre-filled with a liquid such as extracts of cannabidiol (CBD), terpenoids, aromatherapy, and tetrahydrocannabinol. The conical head 82 of the stem 78 is pushed through the aperture 68 in the cap 62 and the weakened portion 58 of the membrane 52 and into the vial 16. The liquid in the vial 16 is transported down conveying tube 78 by the capillary action of either the fiber or ceramic therein and into the vaporization chamber 18. The liquid entering the vaporization chamber comes into contact with the heated wrapping 115 of the ceramic heating coil 104 and is vaporized. The vapor proceeds out the vents 96, 98, within the main housing 14 and is drawn out by the user using the mouthpiece 12.

Figure 17:
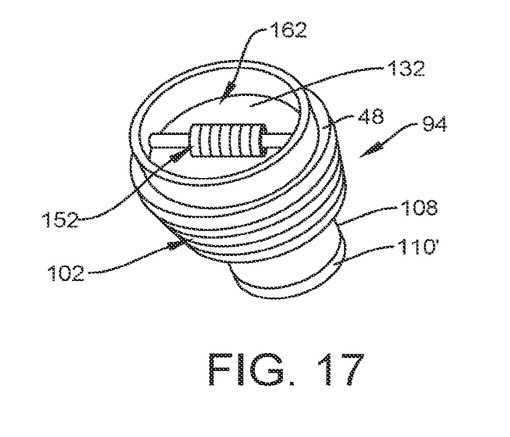
FIG. 17 is a perspective view of an alternate heater for use with the vaporization chamber of FIG. 14.
Figure 20:
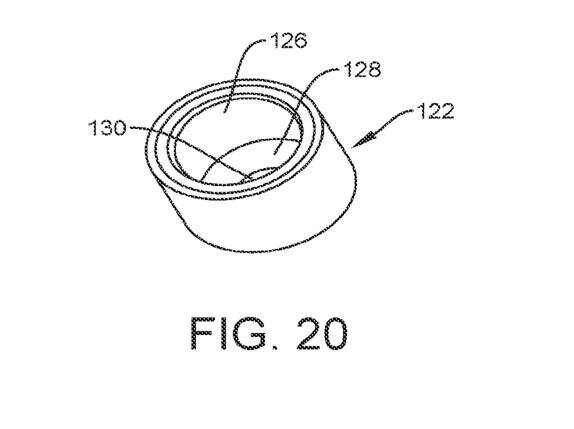
FIG. 20 is a perspective view of a base member of a heater housing of the type disclosed in FIG. 17.
Figure 22:
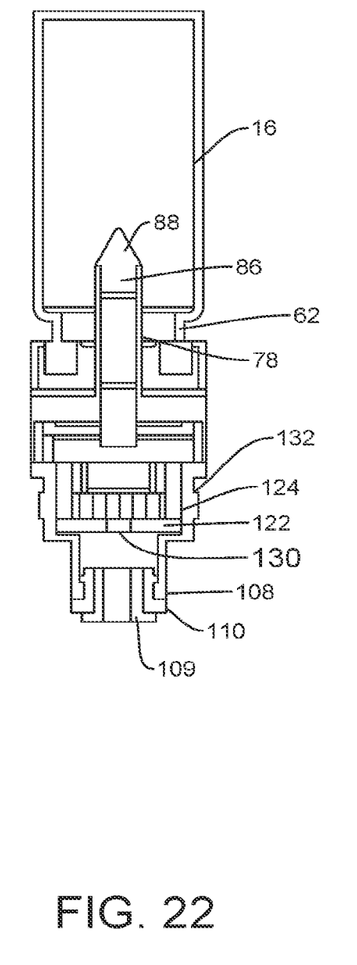
FIG. 22 is a schematic drawing of a vial secured to a conveyance tube of a vaporization chamber and vaporization chamber of the type disclosed in FIG. 17.

A second embodiment of the heating device 94' may comprise a cylindrical heater housing 102', a stem 108', and an insulated plug 110' (FIG. 17, 22). A generally cylindrical base member 122 (FIGS. 17, 20) may have a generally cylindrical side wall 124 open at one end 126 and a closed bottom wall 128 having a centrally disposed aperture 130. The base member 122 is placed within the heating device 94'.

Figure 18:
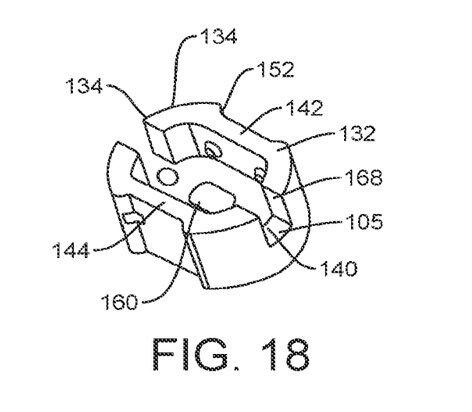
FIG. 18 is a perspective view of a ceramic armature for use in the heater of FIG. 17.
Figure 19:
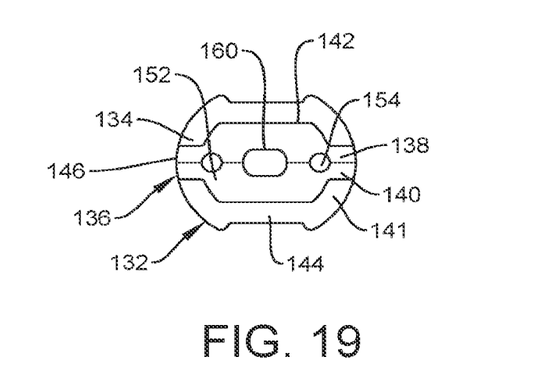
FIG. 19 is a top view of the ceramic armature of FIG. 18.

A U-shaped armature 132 (FIGS. 18, 19) made of ceramic is disposed within the heater housing 102' and inside the base member 122. The respective opposed ends 134, 136 and 138, 140 of the legs 142, 144 of the U-shaped armature 132 are bent toward one another so as to define slots 146, 148 there between. A heated wire, which may be made of Titanium 152 is wrapped about a rod 150 (FIG. 17). The rod 150 may be made of quartz, ceramic, or cotton. The rod 150 wrapped with the wire 152 is placed into the slots 146, 188. The armature 132 is secured to the heating device housing 102.' by any known connecting means which may use two apertures 154, 156 in the armature base wall 158. The wire 152 may be fed through a central aperture 160 in the armature base wall 158 and through the aperture 130 in the bottom wall 12.8 and is connected to a battery contact in the plug 109'. The battery contact is held in position by the insulating plug 110'. The exterior of the armature 132 serves to prevent the extract from passing down below the heating coil 152. In use, the heater 94' receives the extract liquid and the heater 94' vaporizes it so that the vapor travels out of the vaporization chamber housing 72 through the main housing 14 and out through the mouthpiece 12.

Where the rod 150 is made of quartz and a liquid such as a distillate or distillates combined with terpenoids is vaporized, it is found that the resulting vapor has a cleaner taste and is less prone to oxidation. Further, the titanium wire 152 and quartz rod 150 is suitable for thick viscosity extracts of the distillates, CBD distillate, etc.

Figure 23:
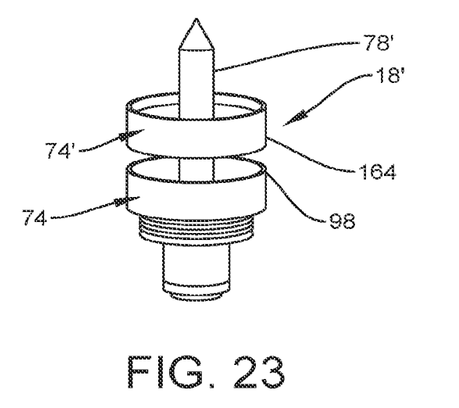
FIG. 23 is a perspective view of another embodiment of the vaporization chamber housing of the type used in connection with the device of FIG. 1.

A second embodiment of the vaporization chamber 18' (FIG. 23) may have a generally cylindrical shape and functions in the same way as the first embodiment 72. The housing 72' of this second embodiment 18' may have a cylindrical wall 164 integrally formed and extending axially upwardly from the upper wall 74' (shown in phantom) of the vaporization chamber 72'. At the radial center of the upper wall 74' is an aperture (not visible) into which the conveying tube 78' is force or snug fit as before. Two slots 96', 98' in the wall of the housing 72' serve to allow vaporized extract to leave the housing. Secured to the housing 72' by threaded engagement or an adhesive may be one of the preciously described heating device 94 or 94'. In this embodiment, the upper end radially extending cylindrical wall 164 serves to support the vial 16 when placed in position.

Figure 24:
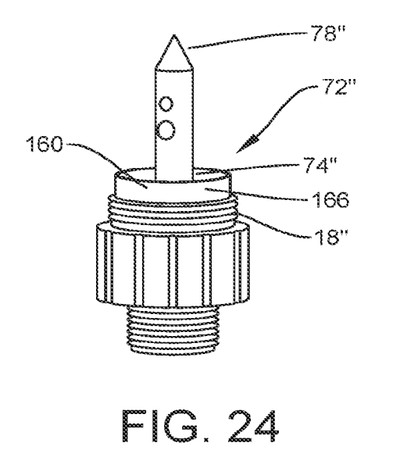
FIG. 24 is a perspective view of another embodiment of the vaporization chamber housing of the type used in connection with the device of FIG. 1.

In a third embodiment of the vaporization chamber 18" (FIG. 24) the radius of the upper end wall 74" is smaller than then the radial extending cylindrical vaporization chamber housing 72". The upper end wall 74" is integrally formed with the cylindrical vaporization chamber housing 72" by a cylindrically radially extending upper end housing 166 to the upper end wall 74". A slot 168 extends through the chamber end wall housing 166 into the vaporization chamber 18". In use, the upper end wall 74", when disposed within the main housing 14, has a relatively smaller diametric dimension than the cylindrically shaped side wall 166 thereby providing a space for the upward flow of the vaporized extract within the main housing 14.

Figure 25:
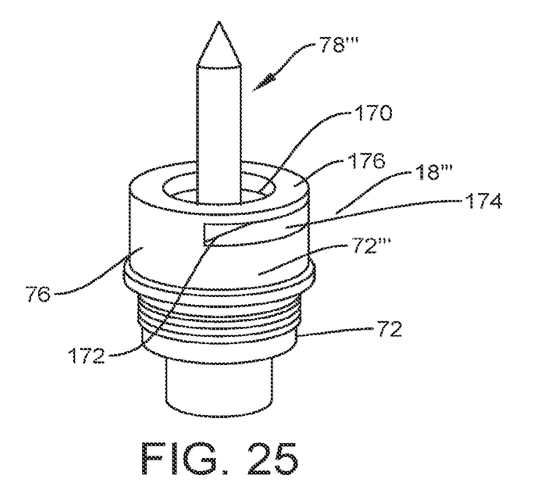
FIG. 25 is a perspective view of another embodiment of the vaporization chamber housing of the type used in connection with the device of FIG. 1.

In a fourth embodiment of the vaporization chamber 18''' there may be provided a generally cylindrical vaporization chamber housing 72" (FIG. 25). A substantially rectangular support member 170 may be integrally formed and attached along its longest dimension 172, to opposed sides to the interior wall (not visible) of the vaporization chamber housing 72" The shorter dimension of the support member 170 is less than its long dimension 172 so that a space 174 is defined between the longest dimension 172 and the interior surface of the vaporization chamber housing 72" the upper end wall 176 is spaced above the support member 170. A hollow conveying tube 78''' may be force fit into an aperture (not shown) in the vaporization chamber housing upper end wall 176. The upper end wall 176 has therethrough a centrally disposed aperture 178. The spacing about the support member 170 permits the contents of the vial 16 to reach the vaporization chamber 18''' should the cap 62 be imperfectly crimped and there is leakage from the vial 16.

Figure 26:
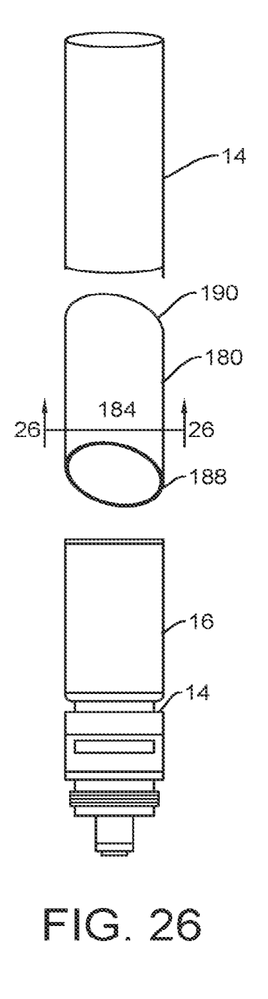
FIG. 26 is a schematic exploded view of an inhalation device with a vent tube.
Figure 27:
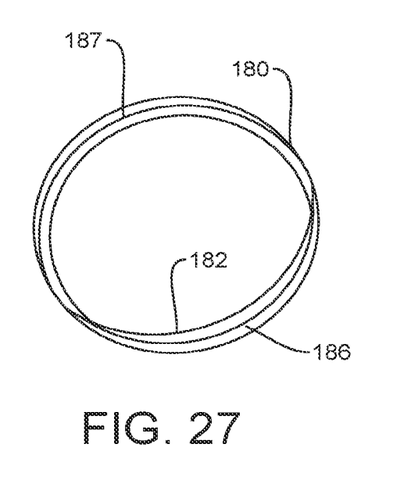
FIG. 27 is a sectional view of the vent tube of FIG. 26 taken along lines 2,6-26 and looking in the direction of the arrows.
Figure 28:
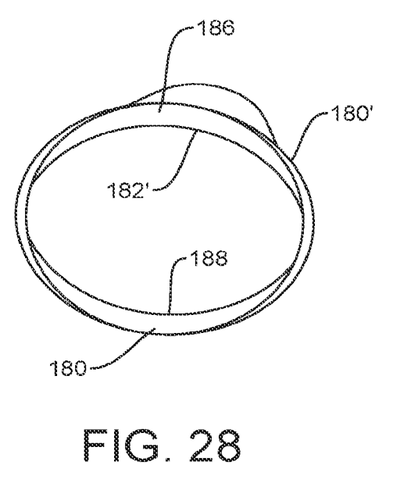
FIG. 28 is a sectional view of an alternate embodiment of the vent tube of FIG. 27.

The examples of electronic inhalation devices, described herein above, may include venting tube 180 (FIGS. 25-27) which may be made of polycarbonate and positioned within the main housing 14 in order to facilitate the flow of vapor from the vaporization chambers 18, 18', 18", or 18''' to the mouthpiece 12. The venting tube 180 which may have a cylindrical outer wall 184 and an inner wall 186. The inner wall 186 which is so spaced so as to describe a curved chord-like space 186. Alternatively, the interior wall 182' of the vent tube 180' may be molded with two spaces 186', 188. The space 186 (FIG. 26) or 186 and 190 (FIG. 27) is open at both ends 188 and 190 of the respective vent tubes 180, -180'. Each vent tube 180, 180' end 186 terminates below the neck 44 of the vial 16 below the exit port to the mouthpiece 12. The vent tube 180, 180' is intended to assure the passage of the vapor from the vaporization chamber to the mouthpiece. Vapor that does not enter the vent tube 180, 180' will pass up between the vent tube and the main house or between the vent tube and the vial 16.

In these examples, there is flexibility for the supplier and the user. Thus, should the vaporization chamber 18, 18', 18", 18''' conveying tube 78, 78' 78", 78''', or heating device 94, 94' in any way fail, it is a relatively simple matter to remove—the vial 16 from the conveying tube 78, 78', 78", 78''' and the membrane 52 will reseal, as is well known. The vial 16 can then be disposed using a replacement vaporization chamber 18, 18', 18", 18''', conveying tube 78, 78', 78", 78''', or heating device 94, 94'. Thus, the liquid stored in the vial 16 will not be lost or wasted.

Upon completion of the use of a vial 16, a user can recycle it and yet retain the inhalation device as compared to those systems in which the heating device or and/other parts of the inhalation device is integral with the liquid container. Further, after use of the disposable vial, the overall inhalation device can be easily cleaned for repeated use. The user, physician or other provider has greater confidence that the encapsulation of the liquid in a sealed container apart from such possible sources of contamination as internal heating elements and the like provides for a long shelf life. Where a liquid is stored in contact with the heating elements, the heating elements can become saturated which will directly effect the time it takes to vaporize as well as the introduction into the stored liquid of pollutants. In addition, because the vial 16 is sealed, a stored liquid is unlikely to be affected by the effects of shipping and handling between the supplier, the dispenser, and the user.

Additionally, the ability to easily disassemble a heating device 94, 94' enables the user to change select the heating coil having the desired materials for the best reaction with the liquid provided by the vial 16.

A safety feature of the crimped cap described above is it is resistant to tampering.

The crimped cap may be color coded or furnished with any other distinguishing indicia so that the contents of any vial can be easily and quickly determined. This can be important where the user has vials of different substances for different purposes or by the dispenser who wishes to more easily distinguishing the contents for more efficient and accurate dispensing to the user.

Another aspect of die inhalation device in its various examples described herein is that when die vial 16 and its contents are kept separate from the vaporizing heating filaments there is less opportunity for degradation of the vial contents by long term contact.

A control module (not shown) can be placed in the battery compartment. Such control modules and their use with batteries in vaporizing devices are well known These control modules can be preprogramed to disconnect the battery after a predetermined number of usages of the inhalation device within a predetermined period of time. Thus, for example, if a physician prescribes five inhales within a twenty-four hour period, a user will find that the device has shut down after the five inhales in one twenty-four hour period (whichever event is earlier) and thus will be prevented overusing the device. The module can also monitor the battery life and provide indication to the user of the status of the battery and also place the battery on standby when the device is not in use.

Another device that is well known for use in the inhalation devices is vibration indicator which provides signals in the form of vibrations to advise the user of the status of the device. For example, the vibration indicator may indicate that a battery is low in power or that the liquid in the vial is almost exhausted. The vibration device is of use for those who are blind or color blind.

What is claimed is:
1. An inhalation device having a mouthpiece, is selectively activated by electrical energy, and in which vapor is obtained from the vaporization of a stored liquid substance which is deliverable to a user upon the user puffing from said inhalation device, said inhalation device comprising:
   a. means for storing the substance, the means comprising a transparent vial having an opening at one end for dispensing the substance, a closure for sealing said open end of said vial comprising a septum and closure cap means for being disposed over said septum and about said end of said vial for sealing said vial open end;
   b. means for heating the substance; said heating means being separate from said storing means;
   c. means for conveying at least a part of the substance from said storing means to said heating means; said heating means being configured to, when activated, produce vapor from the substance and being equipped with a venting tube; and d. means for communicating the vapor from said heating means such that upon the user puffing on said inhalation device, the vapor is delivered to the user, wherein an interior wall of the mouthpiece has a first circumference, wherein an exterior wall of the means for storing the substance has a second circumference, wherein the first circumference and the second circumference are defined by rigid components, and wherein the first circumference is smaller than the second circumference.

2. The inhalation device as recited in claim 1 wherein said vial is made of borosilicate.

3. The inhalation device as recited in claim 1 wherein said septum having a part thereof with a reduced cross-sectional thickness and an annular structure about said reduced cross-sectioned thickness; said reduced thickness being disposed in registry with said vial open end.

4. The inhalation device of claim 3 further comprises:

a. a vaporizing housing; said heating means within said vaporizing housing; said vaporizing housing having a substance receiving aperture therethrough providing access from the exterior to the interior of said vaporizing housing;

b. a hollow conveying tube open at opposed ends with at least one laterally extending tube aperture from the conveying tube exterior into the interior of said tube for permitting the substance in said vial to enter into said conveying tube; one of said conveying tube open ends being secured to a vaporizing housing aperture for conveying the substance through substance receiving aperture and into said vaporizing housing;

c. said conveying tube comprising means for piercing said cap and said septum at said septum reduced cross-sectional thickness; and d. a wicking material within said tube so that the substance in said vial being capable of entering said conveying tube through said tube aperture and being transported by capillary action through said tube aperture and into said vaporization housing.

5. The inhalation device as recited in claim 4 wherein there are at least two laterally extending tube apertures each of different sizes so as to be able to accept stored substances of differing viscosities.

6. The inhalation device as recited in claim 4 wherein said piercing means comprises a conically shaped piercing member and a shaft integrally formed with said conical member; said shaft having free end secured into the end of said conveying tube opposed to said end secured to said substance receiving aperture of said vaporization chamber.

7. The inhalation device as recited in claim 6 wherein said wicking material is made of cotton.

8. The inhalation device as recited in claim 6 wherein said wicking material is made of ceramic.

9. The inhalation device as recited in claim 6 further comprises a device housing; said vial and said vaporizing housing being within said device housing; said device housing having an aperture from the exterior to the interior of said device housing so as to permit the vapor to be drawn from said inhalation device by the user; said device housing having means for channeling the vapor from said vaporizing housing to said aperture.

10. The inhalation device as recited in claim 9 wherein said vaporizing housing having a vapor aperture extending from the exterior of said vaporizing housing to the interior of said vaporizing housing to permit vapor produced by the heating of the substance by said heating means to exit said vaporizing housing.

11. The inhalation device as recited in claim 10 said device housing comprising an exterior wall and at least one interior wall joined to said exterior wall; said exterior wall being spaced from said interior wall and within said device housing interior; said exterior and interior walls defining therebetween a flue; said interior wall of said device housing having two openings within said device housing; said first opening being proximate said vapor aperture in said vaporizing chamber; said second opening being proximate a device housing aperture such that the vapor enters said flue from said vaporizing chamber aperture and exits said flue proximate said housing aperture.

12. The inhalation device as recited in claim 10 further comprises said interior of said device housing having a space between said vapor aperture and a device housing aperture.

13. The inhalation device as recited in claim 12 further comprises a mouthpiece connected to said exterior of said device housing and engaging said device housing aperture such that the user may draw vapor accumulated within said device housing.

14. The inhalation device as recited in claim 11 further comprises a mouthpiece connected to said exterior of said device housing and engaging said device housing aperture such that the user may draw vapor accumulated within said device housing.

15. The inhalation device as recited in claim 14 where in said heating means further comprises:

a. a heating wire;

b. a nonconductive armature secured within said heating housing; said heating wire wrapped about said armature and responsive to the electrical power.

16. The inhalation device as recited in claim 11 is pen-like in configuration.

17. The inhalation device as recited in claim 10 further comprising:

a. said device housing have a generally cylindrically shaped exterior wall and the interior surface of said device housing exterior wall defining therewithin a device housing chamber;

b. said vaporizing housing comprises i. a generally cylindrical shaped exterior wall; the interior surface of said vaporizing chamber exterior wall defining therewithin a hollow space and so dimensioned such that the exterior surface of said vaporizing housing is spaced from said interior surface of said device housing wall; said vapor aperture being at least one slot; and ii. a wall closing one end of said vaporizing housing extending substantially perpendicular to the principal axis of said vaporizing housing; and c. said heating means comprises a heater housing having a generally cylindrically shaped outer wall within said vaporizing housing and enclosing the opposed end of said vaporizing housing opposed to said one end wall and enclosing said device housing.

18. The inhalation device as recited in claim 17 wherein said heating means further comprises a. a heating coil of ceramic within said heater housing and responsive to the electrical power; and b. a protective barrier about said ceramic to prevent the substance from damaging said ceramic.

19. The inhalation device as recited in claim 18 wherein the protective barrier is polypropylene fibers which are needle punched to form an impermeable barrier.

20. An inhalation device having a mouthpiece featuring an aperature, is selectively activated by electrical energy, and in which vapor is obtained from the vaporization of a stored liquid substance which is deliverable to a user upon the user puffing from said inhalation device, said inhalation device comprising:
- means for storing the substance, the means comprising a transparent vial having an opening at one end for dispensing the substance, a closure for sealing said open end of said vial comprising a septum and closure cap means for being disposed over said septum and about said end of said vial for sealing said vial open end;
- means for heating the substance; said heating means being separate from said storing means;
- means for conveying at least a part of the substance from said storing means to said heating means; said heating means being configured to, when activated, produce vapor from the substance and being equipped with a venting tube; and
- means for communicating the vapor from said heating means such that upon the user puffing on said inhalation device, the vapor is delivered to the user,
  - wherein an interior wall of the mouthpiece has a first circumference,
  - wherein an exterior wall of the means for storing the substance has a second circumference,
  - wherein the first circumference and the second circumference are defined by rigid components, and
  - wherein the first circumference is smaller than the second circumference.

* * * * *